United States Patent [19]

Brennan

[11] 4,190,054
[45] Feb. 26, 1980

[54] THERAPEUTIC BANDAGE WITH REMOVABLE HOT OR COLD PACKS

[76] Inventor: H. George Brennan, 10800 Ambazac Way, Bel Air, Calif.

[21] Appl. No.: 860,327

[22] Filed: Dec. 14, 1977

[51] Int. Cl.² .............................................. A61F 7/00
[52] U.S. Cl. .................................... 128/402; 128/163
[58] Field of Search ....................... 128/254, 379–384, 128/399–403, DIG. 15, 163, 165, 166

[56] References Cited

U.S. PATENT DOCUMENTS

| | | | |
|---|---|---|---|
| 919,614 | 4/1909 | Meinecke | 128/399 |
| 1,567,931 | 12/1925 | Epler | 128/399 |
| 2,206,481 | 7/1940 | Luchs et al. | 128/399 |
| 2,288,745 | 7/1942 | Sammis | 128/399 X |
| 2,298,361 | 10/1942 | Freund | 128/399 X |
| 2,715,315 | 8/1955 | Giardini | 128/399 X |
| 3,491,761 | 1/1970 | Baker | 128/402 |
| 3,709,225 | 1/1973 | Sobel | 128/254 |
| 3,822,705 | 7/1974 | Pilotte | 128/379 |
| 3,882,873 | 5/1975 | Arango | 128/402 X |
| 3,889,684 | 6/1975 | Lebold | 128/402 |
| 3,900,035 | 8/1975 | Welch et al. | 128/402 |
| 3,950,789 | 4/1976 | Konz et al. | 128/402 X |
| 4,055,188 | 10/1977 | Pelton | 128/402 |
| 4,081,150 | 3/1978 | Tyson | 128/402 |
| 4,092,982 | 6/1978 | Salem | 128/402 X |

OTHER PUBLICATIONS

"Braces Today;" Pope Foundation, Inc., May. 1954.

*Primary Examiner*—Richard J. Apley
*Attorney, Agent, or Firm*—Philip M. Hinderstein

[57] ABSTRACT

A removable bandage attachable to a body part for entirely covering same, the bandage being made from an elastic material so as to hold the flesh of the body part firmly in place following surgery, a plurality of Velcro strips positioned on the outside surface of the bandage, a flexible fluid retaining envelope having a fluid therein which is heatable or coolable so that the envelope functions as a hot or cold pack, complementary Velcro strips on one side of the envelope to permit attachment of the envelope to the bandage without moving the bandage out of contact with the body part, and a layer of insulating material covering the outside of the envelope for reducing heat loss therefrom.

2 Claims, 4 Drawing Figures

THERAPEUTIC BANDAGE WITH REMOVABLE HOT OR COLD PACKS

BACKGROUND OF THE INVENTION

1. Field of the Invention

The present invention relates to a therapeutic bandage with removable hot or cold packs and, more particularly, to a therapeutic bandage for protecting and holding firmly in place the flesh of a body part and for keeping the body part hot or cold.

2. Description of the Prior Art

Following a variety of different types of surgery on various parts of the body, it is necessary to protect and hold the flesh of the body part firmly in place and to keep the tissues cold. By way of example, these are necessities following cosmetic surgery on the face where it is necessary to hold the facial tissues to prevent sagging and to keep the facial tissues cold to minimize swelling.

Existing therapeutic bandages have a variety of shortcomings. Typically, they are designed for non-surgical purposes, such as to support tissues against sagging during sleep. Typically, they are designed to be only "chin" straps or for other specific parts of the body which does not permit them to support the areas required for surgery such as outside of the eyes, behind the ears, the corners of the mouth, the neck, chin, forehead, etc. In other words, such bandages are not therapeutic.

Most therapeutic masks that are presently available are made of heavy material which holds heat in on the areas covered. The masks also exert excessive pressure on the facial tissues. Typically, they do not make provision for holding a cold pack in place. The same general shortcomings apply to elastic bandages used on other parts of the body for therapeutic purposes.

For a variety of different purposes, devices have been designed for holding a hot or cold pack against a particular body part. Furthermore, bandages have been designed having the capability of attachment of hot or cold packs thereto. However, in all known cases, the hot or cold pack is held directly on the body part through openings in the bandages or by hanging from the bandage. As a result, the area that has the cold pack applied thereto is not held firmly in place and, even if it were, the pressure is removed each time it is necessary to replace the hot or cold pack. This is especially undesirable after facial surgery where the pressure should be retained and the skin should not be contacted during the healing process.

SUMMARY OF THE INVENTION

According to the present invention, these problems are solved by the provision of a therapeutic bandage with removable hot or cold packs. In its preferred embodiment, the present invention includes a bandage designed to support the areas of the face on which cosmetic surgery usually takes place, i.e. outside of the eyes, behind the ears, the corners of the mouth, the neck, the chin, the forehead, etc. The bandage is made from an elastic material so that it protects and holds the facial tissues in place against sagging.

The bandage incorporates a plurality of attachment points located over the outside surface thereof for receipt of specially designed hot or cold packs which are attachable to the various attachment points. The packs are readily attachable and removable from the bandage and are attachable to the outside surface thereof so that attachment or removal does not move the inside surface of the bandage out of contact with the body part protected and held thereby. The particular packs are made of a flexible material which will conform to the contour of the body part. The packs are filled with a material having a high specific heat and are heatable or coolable before use. The packs are covered on one side with a layer of insulating material to inhibit heat loss to the air on the side facing away from the skin.

Briefly, the present invention comprises a removable bandage attachable to a body part for covering same, the bandage being made from an elastic material so as to hold the flesh of the body part firmly in place, a flexible fluid retaining envelope, the fluid therein being heatable or coolable so that the envelope functions as a hot or cold pack, and means for attaching the envelope to the outside surface of the bandage without moving the inside surface thereof out of contact with the body part to apply heat or cold to the body part.

It is therefore an object of the present invention to provide a therapeutic bandage with removable hot or cold packs.

It is a further object of the present invention to provide a therapeutic bandage which protects and holds a body part while simultaneously applying heat or cold thereto.

It is a still further object of the present invention to provide a face mask designed to support the areas of a face on which cosmetic surgery usually takes place.

It is another object of the present invention to provide a face mask which includes means for holding hot or cold packs in contact with those areas on which cosmetic surgery usually takes place.

It is still another object of the present invention to provide a therapeutic bandage which fits different parts of the body which are frequently subject to needing cold applications to reduce swelling and inflammation.

Still other objects, features, and attendant advantages of the present invention will become apparent to those skilled in the art from a reading of the following detailed description of the preferred embodiment constructed in accordance therewith, taken in conjunction with the accompanying drawings wherein like numerals designate like or corresponding parts in the several figures and wherein:

DESCRIPTION OF THE PREFERRED EMBODIMENT

Figure 1:
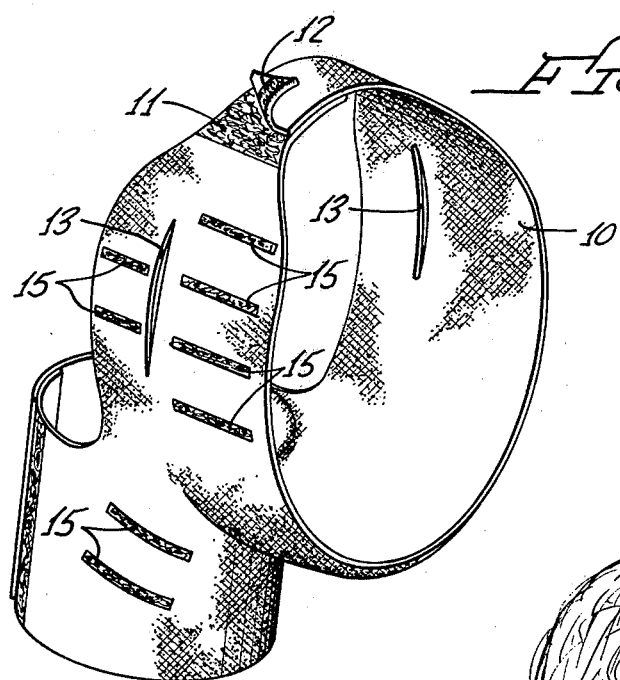
FIG. 1 is a perspective view of a therapeutic bandage constructed in accordance with the teachings of the present invention.
Figure 2:
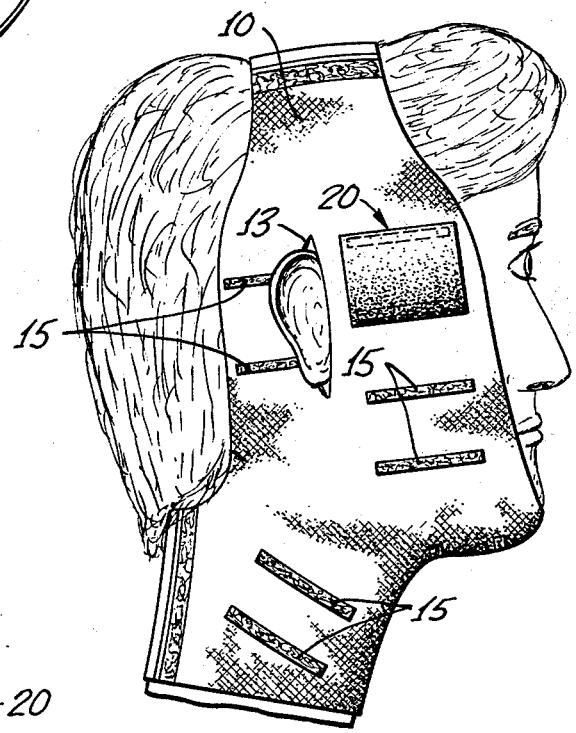
FIG. 2 is a side elevation view of the bandage of FIG. 1 in operative position on the face of a user with a removable hot or cold pack in place.

Referring now to the drawings and, more particularly, to FIGS. 1 and 2, there is shown a removable bandage, generally designated 10, attachable to a body part for entirely covering same. Bandage 10 is made from an elastic material so as to hold the flesh of the body part firmly in place. In the embodiment shown in FIGS. 1 and 2, bandage 10 is in the form of a face mask which is ideally suited for use following cosmetic surgery on the face where it is necessary to hold the facial tissues to prevent sagging. Thus, bandage 10 covers the areas outside of the eyes, behind the ears, the neck, and the chin. The specific embodiment of bandage 10 shown in FIGS. 1 and 2 does not cover the forehead, but obviously it can be so manufactured. Furthermore, while bandage 10 is shown in its preferred embodiment for covering the face, it will be obvious that similar bandages can be made with contours to cover other body parts. Furthermore, bandage 10 may be used not only following surgery but in other situations where it is necessary to support a body part or to reduce swelling and inflammation such as after sprains, bruises, excessive athletic endeavors, etc.

In order to permit bandage 10 to be secured around the face of a user, openings are provided at strategic locations, such as adjacent the back of the neck and along the top of the head, as shown. These openings are provided with suitable fastening means to permit closure of bandage 10 around the face. By way of example, the sides of bandage 10 may overlap above the head and the overlapping end portions may be provided with complementary Velcro strips 11 and 12. Valcro strips are ideally suited for this purpose because they permit attachment in a variety of different locations to permit bandage 10 to adapt to different sizes of heads. Similar Velcro strips would be provided where the sides of bandage 10 overlap behind the neck of a user. The sides of bandage 10 which extend along the face of the use may be conveniently provided with slits 13 for receipt of the ears.

Figure 3:
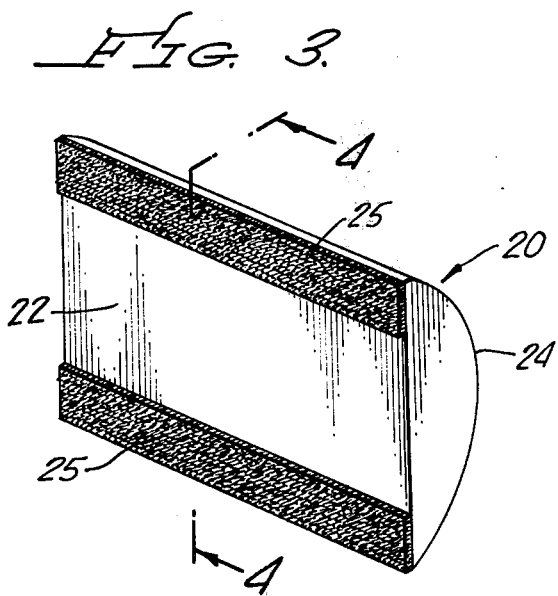
FIG. 3 is a perspective view of a hot or cold pack usable with the bandage of FIG. 1.
Figure 4:
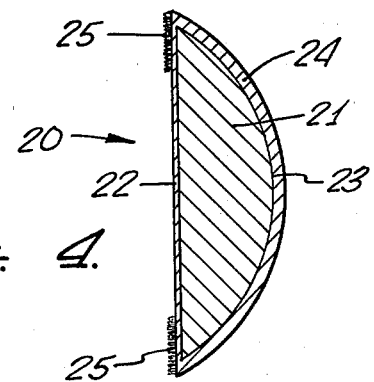
FIG. 4 is a sectional view taken along the line 4—4 in FIG. 3.

As just described, bandage 10 provides a means for covering the areas of the face on which cosmetic surgery usually takes place, bandage 10 being made from an elastic material so as to hold the flesh of the face firmly in place during the healing process. In addition, bandage 10 incorporates means for attachment thereto of hot or cold packs. More specifically, and with reference to FIGS. 3 and 4, the present invention includes a flexible fluid retaining envelope, generally designated 20, having a fluid 21 therein which is heatable or coolable so that envelope 20 functions as a hot or cold pack. Envelope 20 is made from a flexible material which will conform to the contour of the face or other body part. Fluid 21 preferably has a high specific heat, preferably a water-based gel, which may be heated or chilled before use. One side 22 of envelope 20 is preferably flat to provide good surface contact with a body part. The other side 23 of envelope 20 is preferably covered with a layer 24 of insulating material so as to reduce heat loss to the air on the side of envelope 20 facing away from the skin.

The present invention incorporates means for attaching envelope 20 to the outside surface of bandage 10 without moving the inside surface of bandage 10 out of contact with the body part it covers. This is very important following surgery where it is desirable to apply a cold pack to the body part on which surgery has been performed without contacting the body part and without removing the force that bandage 10 applies to the body part. Furthermore, since surgery can be performed at many different locations, all of which are covered by bandage 10, it is important that the attaching means permits attachment of envelope 20 to bandage 10 at any one of many positions over the outside surface of bandage 10.

According to the present invention, the attachment means comprises a plurality of Velcro strips 15 positioned on the outside surface of bandage 10 and covering the locations which would typically require the application of a hot or cold pack. Therefore, Velcro strips 15 will be positioned behind the ears, outside of the eyes, by the corners of the mouth, under the chin, along the neck, etc. Furthermore, each envelope 20 has a plurality of complementary Velcro strips 25 connected to side 22 thereof. While not necessarily required, it is preferable that the spacing between Velcro strips 15 is the same as the spacing between Velcro strips 25.

The use of bandage 10 and envelopes 20 will be obvious from an inspection of FIG. 2. After the surgery has taken place, bandage 10 is secured to the face in the manner described previously. After the fluid 21 within one or more envelopes 20 has been heated or cooled, envelope 20 can be readily attached to any portion of bandage 10 by bringing strips 25 into contact with strips 15. After the heat or cold from envelope 20 has been dissipated, envelope 20 can be readily removed and another envelope 20 attached without moving the inside surface of bandage 10 out of contact with the body part covered thereby.

It can therefore be seen that according to the present invention, the problems discussed hereinbefore have been solved by the provision of a therapeutic bandage 10 with removable hot or cold packs 20. In its preferred embodiment, the present invention includes a bandage designed to support the areas of the face in which cosmetic surgery usually takes place. However, bandages corresponding to bandage 10 may be readily designed to cover the elbow, the shoulders, the knee, the ankle, the hip, etc., any part of the body which is frequently subject to needing hot or cold applications for any purpose.

Bandage 10 is made from an elastic material so that it protects and holds the facial tissues in place against sagging. Bandage 10 incorporates a plurality of attachment points located over the outside surface thereof for receipt of specially designed packs 20 which are attachable to the various attachment points. Envelopes 20 are readily attachable and removable from bandage 10 and are attachable to the outside surface thereof so that attachment or removal does not move the inside surface of bandage 10 out of contact with the body part protected and held thereby.

Envelopes 20 are made of a flexible material which will conform to the contour of the body part. Envelope 20 is filled with a material having a high specific heat which is heatable or coolable before use. Envelopes 20 are covered on side 23 with a layer of insulating material 24 to inhibit heat loss to the air on the side facing away from the body part.

While the invention has been described with respect to a preferred physical embodiment constructed in accordance therewith, it will be apparent to those skilled in the art that various modifications and improvements may be made without departing from the scope and spirit of the invention. For example, while a plurality of Velcro strips 15 on the outside surface of bandage 10 and a plurality of complementary Velcro strips 25 on side 22 of each envelope 20 have been disclosed as the means for attaching envelopes 20 to bandage 10, other methods of attaching envelopes 20 to bandage 10 will be evident to those skilled in the art. Accordingly, it is to be understood that the invention is not to be limited by the specific illustrative embodiment, but only by the scope of the appended claims.

I claim:

1. An article of manufacture comprising:
    a removable bandage attachable to a body part for covering same, said bandage being made from an elastic material so as to hold the flesh of said body part firmly in place;
    a flexible fluid retaining envelope, the fluid therein being heatable and coolable so that said envelope functions as a hot or cold pack; and
    means provided on the outside surface of said bandage for removably and selectively attaching said envelope to said outside surface of said bandage without moving the inside surface thereof out of contact with said body part to apply heat or cold to said body part.

2. An article of manufacture according to claim 1, further comprising:
    a plurality of said attaching means on said outside surface of said bandage to permit attachment of said envelope to said bandage at any one of many positions over said outside surface thereof.

* * * * *